June 20, 1972 W. H. JESSEL, JR., ET AL Plant Pat. 3,212

CHRYSANTHEMUM PLANT

Filed Oct. 12, 1970 2 Sheets-Sheet 1

INVENTORS
WALTER H. JESSEL, JR.,
WILLIAM E. DUFFETT
BY
Oberlin, Maky, Donnelly & Renner
ATTORNEYS

United States Patent Office

Plant Pat. 3,212

Patented June 20, 1972

3,212
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 12, 1970, Ser. No. 80,256
**Int. Cl. A01h *5/00***
U.S. Cl. Plt.—74 1 Claim

The present invention comprises a new and distinct variety of chrysanthemum plant which is a seedling of #54285-7× Delight, an unpatented commercial cultivar. The unnamed parent is identified by such number for breeding purposes by Yoder Brothers, Inc., Barberton, Ohio, the assignee of the present invention.

The new variety is similar in many respects to Tuneful, a well-known commercial variety, having the same characteristics as Tuneful of:

(1) Delayed and uneven flowering response during high temperature periods.

(2) Requires 62° F. minimum night temperature for bud initiation.

(3) Dark green foliage.

(4) Heavy substance of the flowers.

The new variety is distinguished from Tuneful by the following characteristics when grown under identical conditions:

(1) One-half to one inch larger flowers.

(2) An average of 8–12 more flowers per spray on stem.

(3) Five inches to six inches more vigor.

(4) Deeper color.

(5) More responsive to growth regulators.

(6) Provides a very rapid take-off after plating and is ready for pinching 4–7 days earlier.

The new variety was selected from the progeny of the above cross and was asexually reproduced by cuttings at Barberton, Ohio. The new variety has been found to retain its distinctive characteristics through successive propagations.

The new variety when grown in the vincinity of Barberton, Ohio, has a response period of approximately 9 weeks. The response time, blooming period, total vigor and color may vary significantly with varying environmental conditions such as temperature, day length, and light intensity.

The following chart outlines the variation in response experienced in Barberton, Ohio with carbon dioxide injected into the greenhouse atmosphere when applicable when grown for the indicated uses:

| Season | Daisy pompon | Disbudded pot mum | Spray pot mum |
|---|---|---|---|
| Spring | Mid-9 week | Early 9 week | Mid-9 week. |
| October through March | Late 9, early 10 week. | Mid-9 week | Late 9 week. |

Suggested flowering in the northern United States is from April through mid-June and October through mid-November as a daisy pompon, and October through June as a pot mum. In the southern United States from December through April as a daisy pompon and pot mum.

Figure 1:
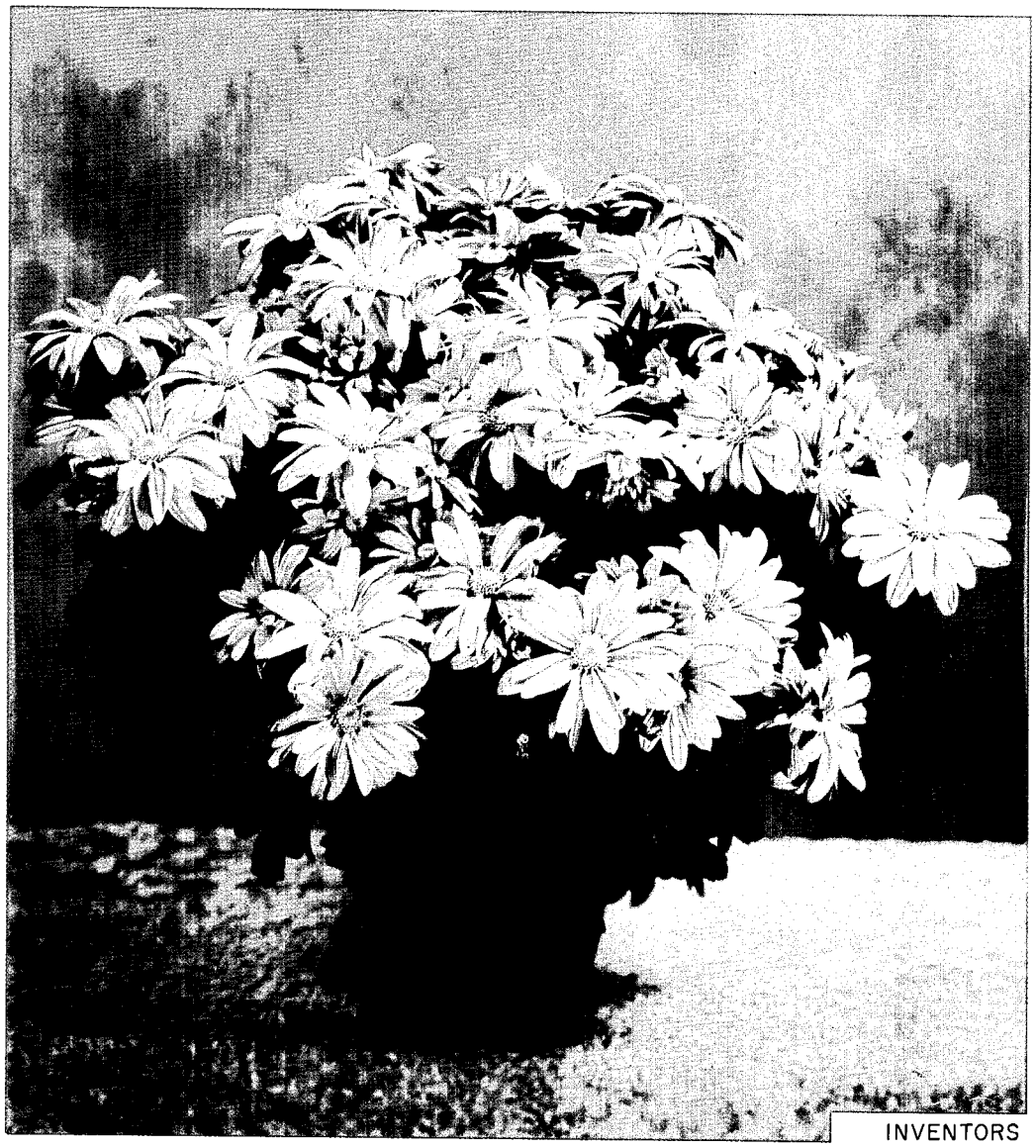
Figure 2:
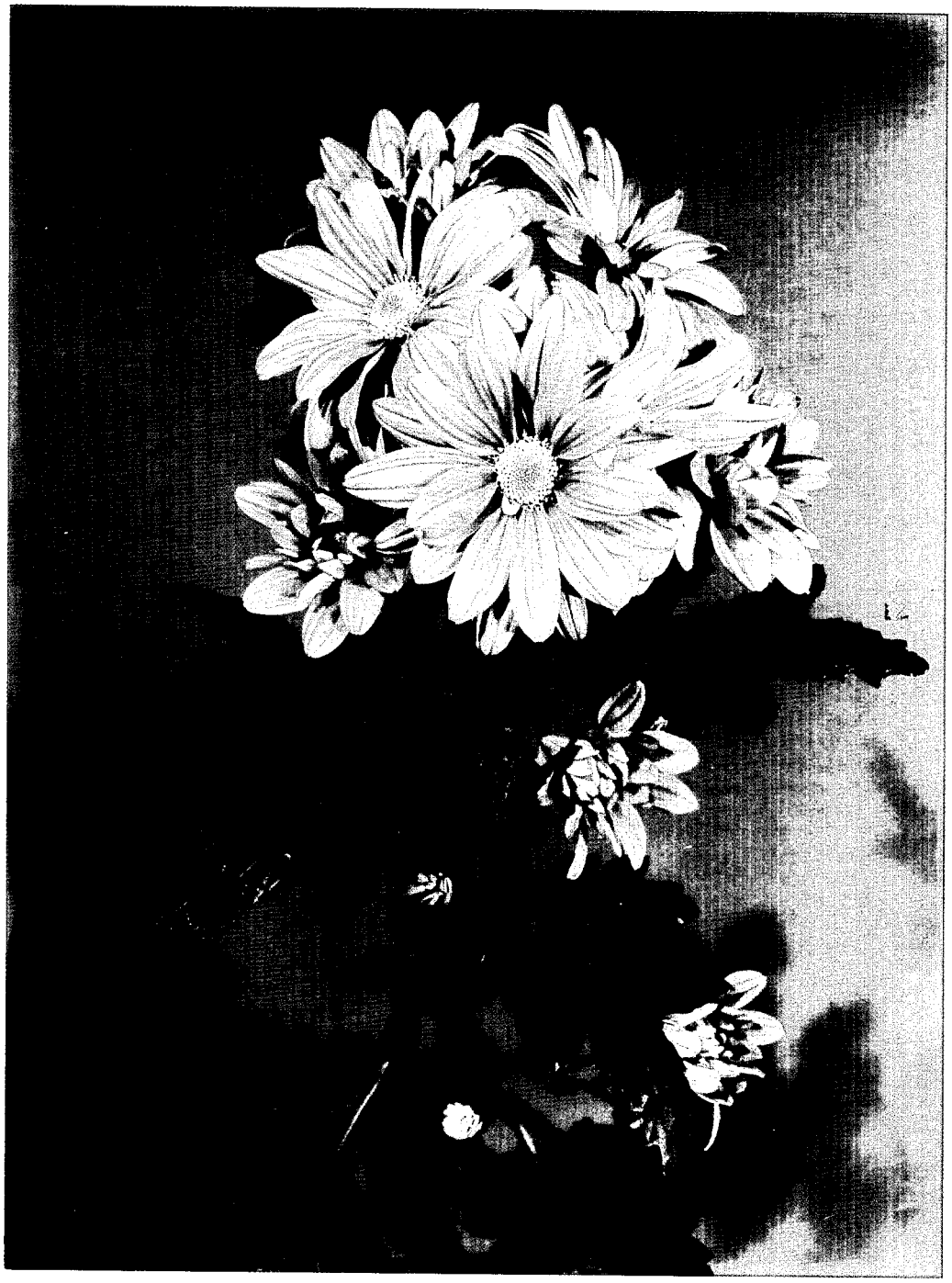

The accompanying drawings show the unique characteristics of the new variety, the colors being as nearly true as possible with color illustrations of this type. FIG. 1 shows new variety as a pot mum, FIG. 2 as a daisy pompon.

The following data is based on observations made of the new variety in a greenhouse in Barberton, Ohio. Color references are to the Munsell Color Book, 1963 Edition, and comparisons have been made in certain instances to the variety Tuneful.

BOTANICAL CLASSIFICATION

*Chrysanthemum morifolium*

| | Aglow | Tuneful |
|---|---|---|
| Bloom: | | |
| Size | 2¾″–4¼″ | 2¼″–3¼″. |
| Fully expanded | 4¼″ | 3¼″. |
| Borne | Clustered on elongated pedicel | Clustered on elongated pedicel. |
| Stems | Elongated pedicels 8″ to 12″ long | Elongated pedicels 6″ to 10″ long. |
| Form | Daisy (single) | Daisy (single). |
| Permanence | 7 to 10 days | 7 to 10 days. |
| Color (Munsell): | | |
| Center of flower | Yellow green, 5GY5/6 to 6.25Y7/12 | Yellow green, 5GY5/6 to 5Y8/14. |
| Base of petals | Approximately red bronze, 10R4/10 to bronze, 5YR6/12 | Approximately yellow bronze, 2.5Y7/10 to bronze, 10R4/8. |
| Inside of petals | Approximately bronze, 8.75YR7/14 to light bronze, 10YR7/12. | Approximately bronze, 10R4/10 to yellow bronze, 2.5Y7/10. |
| Reverse of petals | Yellow green, 5Y8/8 | Approximately light bronze, 10YR7/6. |
| Tonality from a distance | Red bronze | Orange bronze. |
| Discoloration | Light bronze | Light bronze. |
| Petals: | | |
| Texture | Rough | Smooth. |
| Appearance and form | Deeply keeled with ridges tapering to a blunt point | Keeled—tapering to a sharp point. |
| Arrangement | Composite, whorled on a single receptacle | Composite, whorled on a single receptacle. |
| Persistent | Resists shatter | Resists shatter. |
| Fragrance | Typical chrysanthemum | Typical chrysanthemum. |

Reproductive organs:

*Stamen, anthers.*—200+.

*Pollen.*—Abundant to none (functional sterility).

*Arrangement.*—Clustered in center of flower.

*Styles.*—Present in both ray and disc florets.

*Length.*—Short.

*Ovaries.*—At base of petals attached to receptacle.

Plant:

*Form.*—Herbaceous.

*Growth.*—Semi-upright.

*Height, depending on culture.*—34″ to 38″ as a daisy pompon, 12″ to 18″ as a pot mum (Tuneful—28″ to 32″ as a daisy pompon, 12″ to 18″ as a pot mum).

*Spread, depending on culture.*—6″–8″ as a pinched pot plant (Tuneful—4″–6″ as a pinched pot plant).

Foliage:

*Top side.*—Dark green, 10GY2/4.

*Size.*—4½″ long, 2¾″ wide (Tuneful—3¼″ long, 2¼″ wide).

*Quantity.*—Numerous.

*Shape.*—Spatulate lobed.

*Texture.*—Smooth.

*Ribs and veins.*—Prominent.

*Edge.*—Deeply indented.

*Serration.*—Slight serration (Tuneful—moderate serration).

*Underside.*—Light green, 7.5GY4/4.

*Stipules.*—Base of petiole.

We claim:

1. A new and distinct variety of chrysanthemum characterized particularly as to its uniqueness when compared with the cultivar Tuneful by its bright red bronze color which is darker than Tuneful, its greater resistance to fading, its larger flowers, ranging from ½" to 1" larger than Tuneful's, its performance as a cut flower where it is taller and far more productive than the Tuneful varieties, its performance as a pot mum where it establishes itself and is ready for pinching earlier thereby providing a more prolific, fuller pot plant with a greater responsiveness to growth regulators.

No references cited.

ROBERT E. BAGWILL, Primary Examiner

UNITED STATES PATENT OFFICE
CERTIFICATE OF CORRECTION

Patent No. PP-3,212 Dated June 20, 1972

Inventor(s) WALTER H. JESSEL, JR. and WILLIAM E. DUFFETT

It is certified that error appears in the above-identified patent and that said Letters Patent are hereby corrected as shown below:

In column 1, line 11 of the patent, change "#54285-7" to --#54285-A07--.

Signed and sealed this 23rd day of July 1974.

(SEAL)
Attest:

McCOY M. GIBSON, JR.
Attesting Officer

C. MARSHALL DANN
Commissioner of Patents

Dedication

PP. 3,212.—*Walter H. Jessel, Jr.*, Doylestown, and *William E. Duffett*, Akron, Ohio. CHRYSANTHEMUM PLANT. Patent dated June 20, 1972. Dedication filed Feb. 6, 1975, by the assignee, *Yoder Brothers, Inc.* Hereby dedicates to the Public the entire remaining term of said patent. [*Official Gazette July 1, 1975.*]